US010111824B2

(12) United States Patent
Lee et al.

(10) Patent No.: US 10,111,824 B2
(45) Date of Patent: Oct. 30, 2018

(54) COSMETIC EMULSIONS

(71) Applicant: KIMBERLY-CLARK WORLDWIDE, INC., Neenah, WI (US)

(72) Inventors: YoenJung Lee, Yongin-Si (KR); Stacy A. Mundschau, Weyauwega, WI (US); Scott W. Wenzel, Neenah, WI (US); Jeffery R. Seidling, Neenah, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 0 days.

(21) Appl. No.: 15/533,853

(22) PCT Filed: Dec. 29, 2015

(86) PCT No.: PCT/US2015/067833
§ 371 (c)(1),
(2) Date: Jun. 7, 2017

(87) PCT Pub. No.: WO2016/109517
PCT Pub. Date: Jul. 7, 2016

(65) Prior Publication Data
US 2017/0367961 A1 Dec. 28, 2017

Related U.S. Application Data

(60) Provisional application No. 62/097,359, filed on Dec. 29, 2014.

(51) Int. Cl.
| | |
|---|---|
| *A61K 8/73* | (2006.01) |
| *A61K 8/00* | (2006.01) |
| *A61Q 19/00* | (2006.01) |
| *A61K 8/19* | (2006.01) |
| *A61K 8/26* | (2006.01) |
| *A61K 8/27* | (2006.01) |
| *A61K 8/37* | (2006.01) |
| *A61K 8/39* | (2006.01) |
| *A61K 8/86* | (2006.01) |
| *A61K 8/04* | (2006.01) |
| *A61K 8/06* | (2006.01) |

(52) U.S. Cl.
CPC ............ *A61K 8/731* (2013.01); *A61K 8/00* (2013.01); *A61K 8/046* (2013.01); *A61K 8/062* (2013.01); *A61K 8/19* (2013.01); *A61K 8/26* (2013.01); *A61K 8/27* (2013.01); *A61K 8/375* (2013.01); *A61K 8/39* (2013.01); *A61K 8/86* (2013.01); *A61Q 19/00* (2013.01)

(58) Field of Classification Search
None
See application file for complete search history.

(56) References Cited

U.S. PATENT DOCUMENTS

| | | | |
|---|---|---|---|
| 3,856,941 A | 12/1974 | Turner | |
| 4,350,605 A | 9/1982 | Hughett | |
| 4,774,079 A | 9/1988 | Shin et al. | |
| 4,801,447 A | 1/1989 | Gum | |
| 4,983,418 A | 1/1991 | Murphy et al. | |
| 5,085,855 A | 2/1992 | Shore | |
| 5,843,881 A * | 12/1998 | Dubois | A61K 8/046 512/1 |
| 5,876,702 A | 3/1999 | Gers-Barlag et al. | |
| 6,042,815 A | 3/2000 | Kellner et al. | |
| 6,103,250 A | 8/2000 | Brieva et al. | |
| 6,242,396 B1 | 6/2001 | Guillou et al. | |
| 6,261,543 B1 | 7/2001 | Fletcher et al. | |
| 6,419,935 B1 | 7/2002 | Gueret | |
| 6,419,938 B1 | 7/2002 | Riedel et al. | |
| 6,492,326 B1 | 12/2002 | Robinson et al. | |
| 6,685,952 B1 | 2/2004 | Ma et al. | |
| 6,878,805 B2 | 4/2005 | Manoharan et al. | |
| 6,974,799 B2 | 12/2005 | Lintner | |
| 7,157,077 B2 | 1/2007 | Shen | |
| 7,282,197 B2 | 10/2007 | Diec et al. | |
| 7,326,409 B2 | 2/2008 | Lemoine et al. | |
| 7,566,464 B2 | 7/2009 | Belfer | |
| 7,811,594 B2 | 10/2010 | Schreiber et al. | |
| 7,863,417 B2 | 1/2011 | Ziegler et al. | |
| 8,182,828 B2 | 5/2012 | Omura et al. | |
| 8,575,106 B2 | 11/2013 | Santhanam et al. | |
| 8,597,622 B2 | 12/2013 | Lemoine et al. | |
| 8,697,656 B2 | 4/2014 | Fournial et al. | |
| 8,741,357 B2 | 6/2014 | Lintner et al. | |
| 8,758,833 B2 | 6/2014 | Garnier et al. | |
| 8,815,814 B2 | 8/2014 | Bardey et al. | |
| 8,871,717 B2 | 10/2014 | Osborne | |
| 2002/0155080 A1 | 10/2002 | Glenn et al. | |
| 2003/0049218 A1 | 3/2003 | Patel et al. | |
| 2003/0206934 A1 | 11/2003 | Riedel et al. | |

(Continued)

FOREIGN PATENT DOCUMENTS

| | | |
|---|---|---|
| DE | 10140637 A1 | 3/2003 |
| EP | 0717981 B1 | 2/2000 |

(Continued)

OTHER PUBLICATIONS

Silube® J1015-O-812, Water in Oil Emulsifier, Technical Data Sheet, Siltech Corp., Toronto, Ontario, Canada, May 2013, 1 page.

*Primary Examiner* — Susan T Tran
(74) *Attorney, Agent, or Firm* — Kimberly-Clark Worldwide, Inc.

(57) ABSTRACT

Cosmetic emulsions are disclosed that can remain stable even with relatively high salt based cosmetic astringent content. In one aspect, an emulsion can include a water phase including water and a rheology modifier including Microcrystalline Cellulose and Cellulose Gum. The emulsion can also include an oil phase comprising Steareth-2 and Glyceryl Stearate and an emulsifier selected from the group consisting of: Steareth-20, Steareth-21, and combinations thereof. The emulsion can include a salt based cosmetic astringent providing at least about 1.0% of the emulsion by weight.

18 Claims, No Drawings

(56) References Cited

U.S. PATENT DOCUMENTS

| | | |
|---|---|---|
| 2005/0002973 A1 | 1/2005 | Johansson et al. |
| 2005/0053568 A1 | 3/2005 | Aubrun-Sonneville et al. |
| 2005/0058669 A1 | 3/2005 | Krzysik et al. |
| 2005/0100585 A1 | 5/2005 | Patel et al. |
| 2005/0152931 A1* | 7/2005 | SaNogueira ............. A61K 8/06 424/401 |
| 2006/0018855 A1 | 1/2006 | Batista et al. |
| 2006/0045894 A1 | 3/2006 | Brown et al. |
| 2006/0140899 A1 | 6/2006 | Koenig et al. |
| 2007/0218025 A1 | 9/2007 | Schulz et al. |
| 2007/0292359 A1 | 12/2007 | Friedman et al. |
| 2008/0038219 A1 | 2/2008 | Mosbaugh et al. |
| 2008/0253973 A1 | 10/2008 | Tamarkin et al. |
| 2009/0010972 A1 | 1/2009 | Modafari et al. |
| 2009/0047226 A1 | 2/2009 | Teckenbrock et al. |
| 2009/0269374 A1 | 10/2009 | Lee et al. |
| 2010/0008957 A1 | 1/2010 | Mundschau et al. |
| 2010/0008958 A1 | 1/2010 | Mundschau et al. |
| 2011/0010817 A1 | 1/2011 | Theberge et al. |
| 2011/0229536 A1 | 9/2011 | Kvitnitsky et al. |
| 2012/0095115 A1 | 4/2012 | Kawa et al. |
| 2012/0100197 A1 | 4/2012 | Kawa et al. |
| 2012/0128601 A1 | 5/2012 | Behler et al. |
| 2012/0258055 A1 | 10/2012 | Gray et al. |
| 2012/0277313 A1 | 11/2012 | Kwon et al. |
| 2013/0164238 A1 | 6/2013 | Banowski et al. |
| 2013/0336903 A1 | 12/2013 | Fernandez Prieto et al. |
| 2014/0004166 A1 | 1/2014 | Cunningham et al. |

FOREIGN PATENT DOCUMENTS

| | | |
|---|---|---|
| EP | 1714638 A1 | 10/2006 |
| EP | 2143418 A1 | 1/2010 |
| GB | 2069333 A | 8/1981 |
| JP | 4573690 B2 | 11/2010 |
| KR | 10-1355051 B1 | 1/2014 |
| WO | WO 2002/047624 A1 | 6/2002 |
| WO | WO 2004/112739 A1 | 12/2004 |
| WO | WO 2006/028311 A1 | 3/2006 |
| WO | WO 2007/046097 A2 | 4/2007 |
| WO | WO 2012/062755 A2 | 5/2012 |
| WO | WO 2012/174096 A2 | 12/2012 |
| WO | WO 2015/066194 A1 | 5/2015 |
| WO | WO15170063 A1 | 11/2015 |

* cited by examiner

COSMETIC EMULSIONS

TECHNICAL FIELD

The present disclosures relates to cosmetic emulsions and to a method for making stable emulsions with relatively high salt based cosmetic astringent content.

BACKGROUND OF THE DISCLOSURE

Emulsions used on the skin may contain one or more salt based cosmetic astringents. For example, a common salt based cosmetic astringent for an emulsion used on the skin is an aluminum based salt. Common examples of aluminum based salts include Ammonium and Potassium Alum, Aluminum Triphosphate, Sodium aluminum Phosphate, Aldioxa, Aluminum Stearate, Aluminum Distearate Aluminum Sulfate, Aluminum Dimyristate, Aluminum Calcium Sodium Silicate, and Aluminum Citrate. However, if the concentration of salt based cosmetic astringent is high enough in some circumstances, the emulsion will not be stable.

For instance, such emulsions tend to de-emulsify in storage, especially at temperatures encountered in warmer climates. They also de-emulsify when subjected to temperatures that cycle between hot and cold. It is believed that the instability in such emulsions including a salt based cosmetic astringent is due to the high ionic strength of the salts.

What is needed is an emulsion system that is stable in the presence of high concentrations of salt based cosmetic astringents.

SUMMARY OF THE DISCLOSURE

In one embodiment, an emulsion can include a water phase, an oil phase, and a salt based cosmetic astringent. The water phase can include water and a rheology modifier including Microcrystalline Cellulose and Cellulose Gum. The oil phase can include Steareth-2 and Glyceryl Stearate and an emulsifier selected from the group consisting of: Steareth-20, Steareth-21, and combinations thereof. The salt based cosmetic astringent can provide at least about 1.0% of the emulsion by weight.

In another embodiment, an emulsion include a water phase, an oil phase, and a salt based cosmetic astringent. The water phase can include water and a rheology modifier comprising Microcrystalline Cellulose, Cellulose Gum, and Gum Arabic. The oil phase can include Steareth-2 and an emulsifier selected from the group consisting of: Steareth-20, Steareth-21, and combinations thereof. The salt based cosmetic astringent can provide at least about 1% of the emulsion by weight.

DETAILED DESCRIPTION OF THE DISCLOSURE

All of the emulsions of the present disclosure display a stability that has not heretofore been observed. The emulsions do not break over time and are resistant to breaking down under conditions of temperature extremes, particularly elevated temperature. Furthermore, the emulsions of the present invention display stability under conditions of repeated heating and cooling cycles. It is unexpected that the emulsions of the present disclosure display stability over time as well as over temperature elevation and variability.

As used herein, a physically stable emulsion is defined as one that has a consistent appearance and no oil/water phase separation for one month at 50° C., and three months at 40° C. The present disclosure is directed to physically stable emulsions with cosmetic astringent that contain relatively high levels of one or more salt based cosmetic astringents (e.g., about 1% by total weight of the emulsion). For instance, in some preferred embodiments, the emulsions contain aluminum based salts such as Ammonium and Potassium Alum, Aluminum Triphosphate and Sodium Aluminum Phosphate.

As used herein, a salt based cosmetic astringent is defined as salt based cosmetic ingredients intended to induce a tightening or tingling sensation on the skin. Exemplary salt based cosmetic astringents include Ammonium and Potassium Alum, Aluminum Triphosphate, Aluminum Glycinate and Aluminum Phenolsulfate, Alcloxa, Aldioxa, Aluminum Stearate, Aluminum Sulfate and Aluminum Citrate, Sodium Aluminum Phosphate, Sodium Alum, Sodium Aluminum Chlorohydroxy Lactate, Calcium Lactate, Calcium Chloride, Calcium Sulfate Hydrate, Sodium Aluminum Lactate, Zinc Acetate, Zinc Chloride, Zinc Sulfate, Zinc Lactate, Zinc Zeolite, Zinc Phenolsulfonate, and combinations thereof. A salt based cosmetic astringent does not include any anti-perspirant based compounds which are listed on the United States Food and Drug Administration's Anti-Perspirant Monograph (21 C.F.R. §§ 310, 350, and 369. Federal Register Vol. 68, No. 110). Anti-perspirant based compounds listed on the Anti-Perspirant Monograph, and which are not "salt based cosmetic astringents as used herein, include: (a) Aluminum chloride up to 15 percent, calculated on the hexahydrate form, in an aqueous solution nonaerosol dosage form; (b) Aluminum chlorohydrate up to 25 percent; (c) Aluminum chlorohydrex polyethylene glycol up to 25 percent; (d) Aluminum chlorohydrex propylene glycol up to 25 percent; (e) Aluminum dichlorohydrate up to 25 percent; (f) Aluminum dichlorohydrex polyethylene glycol up to 25 percent; (g) Aluminum dichlorohydrex propylene glycol up to 25 percent; (h) Aluminum sesquichlorohydrate up to 25 percent; (i) Aluminum sesquichlorohydrex polyethylene glycol up to 25 percent; (j) Aluminum sesquichlorohydrex propylene glycol up to 25 percent; (k) Aluminum zirconium octachlorohydrate up to 20 percent; (l) Aluminum zirconium octachlorohydrex gly up to 20 percent; (m) Aluminum zirconium pentachlorohydrate up to 20 percent; (n) Aluminum zirconium pentachlorohydrex gly up to 20 percent; (o) Aluminum zirconium tetrachlorohydrate up to 20 percent; (p) Aluminum zirconium tetrachlorohydrex gly up to 20 percent; (q) Aluminum zirconium trichlorohydrate up to 20 percent; and (r) Aluminum zirconium trichlorohydrex gly up to 20 percent.

Particularly preferred salt based cosmetic astringents include Ammonium Alum, Aldioxa, Aluminum Stearate, and Aluminum Citrate. Salt based cosmetic astringents can be supplied at a concentration of about 0.1% to about 10%. One advantage of using salt based cosmetic astringents to other astringents is the dry powdery feel they impart to the formulation and ability to keep the surface of the skin dry, particularly aluminum based salts.

It is believed that salt based cosmetic astringents taken alone can significantly disrupt the stability of emulsions. Not to be bound by theory, but it is believed that this instability is due to the high ionic strength of the salt based cosmetic astringents. The emulsions of the present disclosure can include a relatively high level of one or more salt based cosmetic astringents, yet still remain stable. In some embodiments, a salt based cosmetic astringent can provide at least about 1.0% of the emulsion by weight. In some embodiments, a salt based cosmetic astringent can provide between about 1.0% and about 15% of the emulsion by weight. In some embodiments, a salt based cosmetic astringent can provide at least about 3.0% of the emulsion by weight. In still other embodiments, a salt based cosmetic astringent can provide at least about 5.0% of the emulsion by weight. In other embodiments, a salt based cosmetic astringent can provide at least about 8.0%, or at least about 10% of the emulsion by weight.

When combined with the appropriate water phase thickeners or co-emulsifiers using the process of the present disclosure, Steareth-2 and Steareth-20 can serve to stabilize emulsions including salt based cosmetic astringents. For example, in one aspect, the combination of Steareth-20 and Steareth-2 with Gum Arabic and Microcrystalline Cellulose with Cellulose Gum produces a stable emulsion that includes about 5% Aluminum Sulfate by weight of the emulsion. In another aspect, the combination of Steareth-20, Steareth-2 and Glyceryl Stearate with Microcrystalline Cellulose with Cellulose Gum produces a stable emulsion that includes 5% Aluminum Sulfate by weight of the emulsion.

However, the process by which the emulsions are made affects long-term physical stability. The process of the present disclosure includes making the emulsion before adding salt based cosmetic astringents, such as Aluminum salts, thereto. Adding salt based cosmetic astringents to the composition before or during emulsion formation results in an unstable emulsion.

Unexpectedly, the emulsions of the present disclosure were found to be physically stable even though (1) Microcrystalline Cellulose alone precipitates in the presence of 5% Aluminum Sulfate Hydrate, (2) Gum Arabic alone precipitates in the presence of 5% Aluminum Sulfate Hydrate, and (3) the emulsion is not stable without thickeners. The present disclosure provides emulsions that include two ingredients that are each unstable when combined with a salt based cosmetic astringent concentrations of at least about 5%, and combines the ingredients in a way that renders the final composition stable.

In some embodiments, the emulsions can be sprayable. As used herein, the term "sprayable" refers to the ability to spray the emulsions with a hand-pump spray bottle, a hand-squeeze spray bottle, pressurized aerosol cans, or similar devices. For the purposes of this invention, "sprayable" emulsions were those that are able to dispense through the Calmar Mark VI® dispenser commercially produced by MeadWestvaco Corporation. The specifications of the spray head of this dispenser are a 20 mm cap with 410 thread, an overall spray volume of 0.16 cc, a spray diameter of 0.057 inches and a dip tube of 2.75 inches. The formulation was loaded into a 2 oz. Boston Round bottle available from Poly-Tainer Inc. (20/410 thread). If the formulation was able to disperse from the package within 10 pumps, the formulation is deemed as "sprayable," as the term is used herein. Other than the pressure applied from the manual depression of the pump, no other pressure is present within the packaging (i.e. aerosolized, pressurized CO2, etc).

In some embodiments, the formulation of the present disclosure can be sprayable. The formulation is dispensed through a hand-held spray dispenser by pressing a dispensing button to spray the formulation onto the skin. In some embodiments, preferred formulations produce a v-shaped pattern of the formulation upon spraying that give droplets upon the skin. Of course, it is contemplated that other conventional spray dispenser mechanism can be used to dispense the skin protectant formulation, including, but not limited to, aerosol or pressurized propellant dispensers, motor driven pump dispensers, and other dispensers using manual spray pump mechanisms. In some embodiments, an emulsion can be sprayable and have a viscosity of about 1 to about 15,000 cps, or about 1 to about 10,000 cps, or about 500 to 8,000 cps.

In a preferred embodiment, the formulations of the present disclosure may be utilized with a continuous spray dispenser. Continuous spray, or continuously sprayable, technology is meant to indicate that the formulation provides any-angle spraying and uniform coverage. An example of a continuous spray dispenser would include a flexible, expandable container adapted to receive the skin protectant formulation. The flexible container is removable surrounded by a rigid exterior housing or canister, which is provided with an air-tight seal. The canister is sealed prior to filling the flexible container with the formulation, so that air is trapped within the canister in the volume unoccupied by the flexible container. When the flexible container is filled with the formulation, the container expands, thereby compressing the air within the canister. While maintaining complete separation from the formulation, this compressed air acts as a propellant. The compressed air then acts against the flexible container to uniformly propel the formulation from the container. In this example, there is no need to pump the spray like conventional spray dispensers to distribute the formulation onto skin. This is advantageous in limiting pain for those with limited dexterity or arthritis.

In another exemplary continuous spray dispenser, the container may include a pump that is integral with the cap on the dispenser. In this example, the air is compressed in the canister not when sealing the canister, but by pumping air into the canister to provide compressed air as a propellant. The compressed air added by a consumer then acts against the flexible container to uniformly propel the skin protectant formulation out of the container.

Continuous spray technology is well known in the art. Suitable commercially available continuous spray dispensers for use with the skin protectant formulation can include, for example, the 12HS Dry Spray Dispenser commercially available from Rexam Airspray or the bag-on-valve dispenser commercially available from ColepCCL.

Emulsifiers:

Suitable emulsifiers that can produce a stable emulsion with water phase thickeners include: a combination of EMALEX 602 (Steareth-2)/EMALEX 620 (Steareth-20) and combination of EMALEX 602/EMALEX 620/CUTINA GMS (Glyceryl Stearate). In addition to emulsifiers, surfactants such as fatty alcohols Cetyl alcohol and/or Stearyl alcohol can be used as viscosity increasing agents.

It is noted that not all emulsifiers will produce a stable emulsion with water-based thickeners. The following emulsifiers, used either alone or in combination, failed to produce a physically stable emulsion when combined with or without the thickeners outlined below and 5% Aluminum based Salt: ARLACEL 165 (Glyceryl stearate, PEG-100 stearate), CERALUTION H (Behenyl alcohol, Glyceryl stearate, Glyceryl stearate citrate, Disodium ethylene dicocamide PEG-15 disulfate), DERMOFEEL EASYMULS (Sunflower seed acids, Polyglyceryl-3 esters citrate, *Helianthus annuus* (sunflower) seed oil), EMALEX 840 (PEG-40 stearate), EMALEX HC-60 (PEG-60 hydrogenated castor oil), EMALEX SEG-07 (Glyceryl stearate, PEG-100 stearate), EMULGADE PL 68/50 (Cetearyl glucoside, Cetearyl alcohol), EMULGADE SUCRO (Sucrose polystearate, Hydrogenated polyisobutene), EUMULGIN SG (Sodium Stearoyl Glutamate), EUMULGIN SML 20 (Polysorbate 20), INC- ROQUAT TMS-50 (Behentrimonium Methosulfate, Cetyl Alcohol, Butylene Glycol), and TWEEN 60 (Polysorbate 60).

Thickeners:

Thickeners affect the viscosity of the emulsion and help prevent oil droplets from coalescing, leading to emulsion instability. As used herein, a thickener can also be referred to as a rheology modifier. Water phase thickeners include: ARAGUM 3173 (Xanthan gum, Guar gum, Propylene glycol alginate), AVICEL PC 611 (Microcrystalline cellulose, Cellulose gum), BENTONE GEL CAO V (*Ricinus communis*, Stearalkonium hectorite, Propylene carbonate), KRUCEL HPC (Hydroxypropyl cellulose), NATPURE Gum (Gum Arabic), NATROSOL HEC (Hydroxyethyl cellulose), and VANZAN NF (Xanthan gum). It is noted that gums such as Xanthan Gum, Guar Gum, Gum Arabic, etc. tended to thicken with the addition of the salt based cosmetic astringent of Aluminum Sulfate Hydrate. Celluloses or minerals used alone precipitated with the addition of the salt based cosmetic astringent of Aluminum Sulfate Hydrate. However, a combination of Gums and Celluloses/Minerals demonstrated better emulsion stability and desirable viscosities.

Method:

In one aspect, the present disclosure includes a method for making a stable emulsion. Shown in TABLE A are three different aspects of the present disclosure where the water, Glyceryl Stearate, Aldioxa, and Aluminum Stearate are variable in amount. These sample emulsions were prepared using the following method.

Referring to TABLE A, a water phase is created by adding water soluble PART A ingredients (Methylparaben, Chlorphenesin, Microcrystalline Cellulose to water as it is heated to a temperature of 75 degrees Centigrade (° C.). An oil phase is created by blending the PART B ingredients: Sunflower oil, Steareth-2, Steareth-21, Glyceryl Stearate and Aluminum Distearate. Oil phase ingredients are mixed constantly while they are being heated to 75° C. Once both phases reach 75° C., Part B is added to Part A and homogenized at 5000 rpm for 5 minutes using a Silverson Homogenizer. The emulsion is returned to propeller based mixing until it cools to 35° C. or lower. The Aluminum Citrate and Ammonium Alum are added to the formulation with the pH being adjusted to 5.25 using sodium hydroxide, as shown in Part C.

TABLE A

| Trade Name | INCI Name | Batch 1 Weight (%) | Batch 2 Weight (%) | Batch 3 Weight (%) |
| --- | --- | --- | --- | --- |
| Part A | | | | |
| Water | Water | 74 | 72 | 73 |
| COSEPT M | Methylparaben | 0.3 | 0.3 | 0.3 |
| ELSTAB CPN | Chlorphenesin | 0.2 | 0.2 | 0.2 |
| AVICEL 611 | Microcrystalline Cellulose and Cellulose Gum | 1 | 1 | 1 |
| Part B | | | | |
| RITA SSO | Sunflower Oil | 4 | 4 | 4 |
| BRIJ-2 | Steareth-2 | 1.5 | 1.5 | 1.5 |
| BRIJ-21 | Steareth-21 | 3 | 3 | 3 |
| CUTINA GMS | Glyceryl Stearate | 2 | 2 | 2 |
| Aldioxa | Aldioxa | 0 | 0 | 1 |
| Dub SA | Aluminum Distearate | 1 | 3 | 1 |
| Part C | | | | |
| Aluminum Citrate | Aluminum Citrate | 1.5 | 1.5 | 1.5 |
| Ammonium Alum | Ammonium Alum | 5 | 5 | 5 |

TABLE A-continued

| Trade Name | INCI Name | Batch 1 Weight (%) | Batch 2 Weight (%) | Batch 3 Weight (%) |
| --- | --- | --- | --- | --- |
| Sodium Hydroxide (20%) | Sodium Hydroxide | 6.5 | 6.5 | 6.5 |

Optional Ingredients:

(a) pH Adjusting Agent

The emulsions of the present disclosure may further include a pH-adjusting agent. Such agents are desirable for the creation of emulsions having a pH at or near that of human skin. Therefore, the pH can be typically be adjusted as necessary so that the emulsions of the present disclosure can have a pH of from 4 to 7, or more desirably, from 4.5 to 6.5. The pH can be adjusted by adding one or more pH-adjusting agents in an amount effective to provide such pH values ("effective amount"). Agents that may be used to adjust the pH of the emulsions include organic and inorganic acids and bases.

Acid pH-adjusting agents include organic acids which are relatively non-irritating. Such acids include malic acid, citric acid acetic acid, propionic acid, oxalic acid, glycolic acid, malonic acid, lactic acid, succinic acid, tartaric acid, aspartic acid, maleic acid, glutaric acid, glutamic acid, gluconic acid, sorbic acid, benzoic acid, ascorbic acid, salicylic acid and mixtures thereof. In one aspect of the present disclosure, a desirable pH-adjusting agent is malic acid.

The amount of the pH-adjusting agent that is employed depends on the equivalent weight of the pH-adjusting agent and the desired pH. Typically, the pH-adjusting agent is used in an amount of from about 0.05% to about 0.5% by weight of the emulsion. Desirable emulsions of the present disclosure include from about 0.1% to about 0.5%, and typically about 0.2% to about 0.3% of the pH-adjusting agent by weight of the emulsion.

(b) Preservatives

The emulsions of the present disclosure may further include one or more preservatives. Preservatives function in one or more ways to improve the shelf life of the emulsions and products incorporating same. For example, the preservative may be an anti-microbial agent, an anti-bacterial agent, an anti-fungal agent, or a combination thereof.

Preservatives herein include, but are not limited to, benzethonium chloride, benzisothiazolinone, benzoic acid, benzyl alcohol, 2-Bromo-2-nitropropane-1,3-diol, butylparaben, caprylyl glycol, chlorhexidine digluconate, DMDM hydantoin, diazolidinyl urea, dehydroacetic acid, ethylparaben, iodopropynyl butylcarbamate, methylchloroisothiazolinone, methylisothiazolinone, methyldibromo glutaronitrile, methylparaben, pentylene glycol, phenethyl alcohol, phenoxyethanol, propylparaben, polyaminopropyl biguanide, quaternium-15, salicylic acid, sodium benzoate, sodium methylparaben, sodium dehydroacetate, thymol, triclosan and mixtures thereof.

In one aspect of the disclosure, benzoic acid, with or without phenoxyethanol, is effective in preventing the growth of a wide variety of microbes and fungi.

An anti-microbial agent may be used in an amount that is effective to provide desired shelf life (storage stability, i.e., microorganisms do not grow to a significant extent) (herein alternatively referred to as "an effective amount"). This includes demonstrating sufficient anti-microbial activity in accordance with United States Pharmacopeia test entitled "Microbial Test, Antimicrobial Preservative-Effectiveness".

(c) Chelating Agent

The emulsions of the present disclosure may contain one or more chelating agents. The chelating agent tends to bind metals (e.g., calcium ions, magnesium ions) that may be present in the emulsion so as to enhance the efficiency of the emulsifier and the anti-microbial agent. Thus, the chelating agent may be considered to provide a level of anti-microbial activity to function as a preservative. The chelating agent may be used in an amount that is effective to bind the aforementioned metals (hereinafter alternatively referred to as an "effective amount"), typically an amount ranging from about 0.01% to about 0.2% by weight of the emulsion. Particularly preferred emulsions include from about 0.05% to about 0.2% by weight of the emulsion, more preferably from about 0.05% to about 0.10% by weight of the emulsion. Chelating agents and their use in personal cleansing emulsions are well known in the art. Exemplary chelating agents include disodium EDTA, trisodium EDTA, tetrasodium EDTA, and tetrasodium iminodisuccinate.

(d) Emollients

In one embodiment, the emulsions can optionally include one or more emollients, which typically act to soften, soothe, and otherwise lubricate and/or moisturize the skin. Suitable emollients that can be incorporated into the compositions include oils such as Ethylhexyl Stearate (Cetiol® 868, BASF), Ethylhexyl Isostearate (Dub ISO, Stearinerie Dubois Fils), C12-15 Alkyl Ethylhexanoate (Hetester FAO, Bernel Chemical Company), C12-15 Alkyl Lactate (Ceraphyl® 41, Ashland Inc.), Caprylic/Capric Glycerides (IM-WITOR® 742, Cremer Oleo), Caprylic/Capric Triglycerides (Crodamol GTCC, Croda, Inc.), Cetyl Esters (Crodamol SS, Croda, Inc.), Cetearyl Isononanoate (Cetiol® SN, BASF Corporation), Cetearyl Dimethicone (Botanisil® CD-16, Botanigenics, Inc.), Cetyl Dimethicone (Abil® Wax 9801, Evonik Industries AG), Coco-Caprylate (Cetiol® C5, BASF Corporation), C12-15 Pareth-3 Benzoate (Dermol® 25-3B, Alzo International), Diethyl Sebacate (Pelemol® DES, Phoenix Chemical, Inc.), Diisostearyl Fumarate (Schercemol DISF Ester, Lubrizol Advanced Materials, Inc.), *Helianthus Annuus* (Sunflower) Seed Oil (Florasun® 90, Floratech), Isodecyl Laurate (Isostearene, Vevy Europe SpA), Lauryl Lactate (Ceraphyl® 31, Ashland Inc.), Octyldodecanol (Isofol 20 Alcohol, Sasol Germany GmbH Hamburg) Olive Oil PEG-7 Esters (Olivem® 300, B&T S.r.l.) PEG-75 Meadowfoam Oil (Meadowsol® 75:75, Elementis Specialties), Perfluorononylethyl Carboxydecyl Lauryl Dimethicone (Pecosil® FST-412, Phoenix Chemical, Inc.), Polyglyceryl-2 Isostearate (Cithrol PG21IS, Croda Europe, Ltd.), Tridecyl Stearate (Hest TDS, Global Seven Inc.), alkyl dimethicones, alkyl methicones, alkyldimethicone copolyols, phenyl silicones, alkyl trimethylsilanes, dimethicone, dimethicone crosspolymers, cyclomethicone, Lanolin and its derivatives, fatty esters, glycerol esters and derivatives, propylene glycol esters and derivatives, alkoxylated carboxylic acids, alkoxylated alcohols, fatty alcohols, and combinations thereof.

The emulsions may include one or more emollients in an amount of from about 0.01% (by total weight of the emulsion) to about 20% (by total weight of the emulsion), or from about 0.05% (by total weight of the emulsion) to about 10% (by total weight of the emulsion), or from about 0.10% (by total weight of the emulsion) to about 5% (by total weight of the emulsion).

(e) Other

The emulsions of the present disclosure may optionally include other ingredients, e.g., fragrance; skin soothing aids such as aloe, lavender, chamomile, green tea, calendula, etc.; skin moisturizers (humectants) such as glycerin, propylene glycol, betaine, and hydroxyethyl urea; or emollients other than those previously described; powders and the like.

In one aspect, a fragrance is added in a concentration range of 0.05% to 4.0% by total weight of the emulsion. In another aspect, the fragrance is added in a concentration of 1.20% by total weight of the emulsion.

Applications:

The emulsions may be applied to the skin as a spray or a cream. The sprayable embodiments can be sprayed using equipment including a pump spray, squeeze spray, and pressurized aerosols, or any other suitable equipment.

Additionally, it is believed that the emulsions may be dispensed in a wipe and applied to the skin through the wipe. The wipe may have a cellulosic structure, such as a tissue, a non-woven structure, foam or a combination thereof that has a one-ply or that has a multi-ply structure, as is known by one of ordinary skill in the art. Suitable wipe substrates include conventional nonwoven materials, homogeneous paper, through-air-dried paper, a differential-density paper, or a differential-basis weight paper or foam.

EXAMPLES

Compositions 1 and 2 are formulations that include emulsifying surfactants, thickeners (rheology modifiers), and salt based cosmetic astringents in the form of Aluminum-based salts. These emulsions were prepared in a manner consistent with the methodology outlined in the Method section above, and were physically stable.

Example Composition 1

TABLE B

| Trade Name | INCI NAME | % wt |
|---|---|---|
| Part A | | |
| Water | Water | QA |
| AVICEL PC 611 | Microcrystalline Cellulose and Cellulose Gum | 0.80 |
| NATPURE GUM | Gum Arabic | 0.50 |
| VERSENE NA2 | Disodium EDTA | 0.10 |
| ALKAMULS PSML-20 | Polysorbate-20 | 1.00 |
| RITA Glycerin USP 99.7% | Glycerin | 2.00 |
| Part B | | |
| EMALEX 620 | Steareth-20 | 1.33 |
| EMALEX 602 | Steareth-2 | 2.66 |
| LANETTE O | Cetearyl Alcohol | 0.25 |
| SNOW WHITE Petrolatum USP | Petrolatum | 20.00 |
| LANETTE 18 | Stearyl alcohol | 0.50 |
| Part C | | |
| Aluminum Sulfate Hydrate | Aluminum Sulfate Hydrate | 5.00 |
| Phenoxetol | Phenoxyethanol | QA |
| Sodium Hydroxide | Sodium Hydroxide | QA |

Example Composition 2

TABLE C

| Trade Name | INCI NAME | % wt |
|---|---|---|
| Part A | | |
| Water | Water | QA |
| AVICEL PC 611 | Microcrystalline cellulose and Cellulose Gum | 1.0 |

TABLE C-continued

| Trade Name | INCI NAME | % wt |
|---|---|---|
| NIPAGIN M | Methyl paraben | 0.2 |
| MICROCARE OHB | Propyl paraben | 0.1 |
| ZEMEA PROPANEDIOL | 1,2-propanediol | 3.0 |
| Part B | | |
| EMALEX 620 | Steareth-20 | 3.0 |
| EMALEX 602 | Steareth-2 | 1.50 |
| LANETTE 18 | Stearyl Alcohol | 1.2 |
| XIAMETER PMX-0245 | Cyclopentasiloxane | 0.3 |
| CUTINA GMS | Glyceryl Stearate | 2.0 |
| Part C | | |
| Aluminum Sulfate Hydrate | Aluminum Sulfate Hydrate | 5.0 |
| Phenoxetol | Phenoxyethanol | 0.4 |

Experimental Data:

For this experiment, three base formulations were prepared per Table D below. The quantity of water and the quantity of Glyceryl Stearate were varied. An amount of Aluminum Citrate was added to each base per Table E below. The viscosity of the resulting emulsions is recorded if it was stable. As can be seen, only one emulsion was stable at each of the four conditions under which it was tested for stability. That is, Base 3 with the addition of 8 percent Aluminum Citrate by weight was the only emulsion that was found to be stable at room temperature, 40° C., and 55° C. In addition, this emulsion was stable after three freeze/thaw cycles.

TABLE D

| Trade Name | INCI Name | Base 1 Weight (%) | Base 2 Weight (%) | Base 3 Weight (%) |
|---|---|---|---|---|
| Part A | | | | |
| Water | Water | 88 | 87 | 86 |
| COSEPT M | Methylparaben | 0.3 | 0.3 | 0.3 |
| ELSTAB CPN | Chlorphenesin | 0.2 | 0.2 | 0.2 |
| AVICEL 611 | Microcrystalline Cellulose and Cellulose Gum | 1 | 1 | 1 |
| Part B | | | | |
| RITA SSO | Sunflower Oil | 4 | 4 | 4 |
| BRIJ-2 | Steareth-2 | 1.5 | 1.5 | 1.5 |
| BRIJ-21 | Steareth-21 | 3 | 3 | 3 |
| CUTINA GMS | Glyceryl Stearate | 2 | 3 | 4 |

TABLE E

| Base | Aluminum Citrate (%) | 55° C. (cP) | Freeze/Thaw (cP) | Room Temperature (cP) | 40° C. (cP) |
|---|---|---|---|---|---|
| 1 | 2 | — | — | — | — |
| 1 | 4 | — | 5120 (6.59) | — | — |
| 1 | 6 | — | — | — | — |
| 1 | 8 | — | — | — | — |
| 1 | 10 | — | — | — | — |
| 1 | 12 | — | — | — | — |
| 2 | 6 | 13867 | — | 7647 | 5.4 |
| 2 | 8 | 9600 | — | 8533 | 5.28 |
| 2 | 10 | 8533 | — | — | — |
| 2 | 12 | — | — | — | — |
| 3 | 6 | 5333 | — | 6400 | 5.54 |
| 3 | 8 | 6400 | 5333 | 14933 | 5.25 |

Note:
Only data related to a stable result are reported.

EMBODIMENTS

Embodiment 1

An emulsion comprising: (a) a water phase comprising water and a rheology modifier comprising Microcrystalline Cellulose and Cellulose Gum; (b) an oil phase comprising Steareth-2 and Glyceryl Stearate and an emulsifier selected from the group consisting of: Steareth-20, Steareth-21, and combinations thereof; and (c) a salt based cosmetic astringent comprising at least about 1.0% of the emulsion by weight.

Embodiment 2

The emulsion of embodiment 1, wherein the rheology modifier comprises about 0.01% to about 2.0% of the emulsion by weight.

Embodiment 3

The emulsion of embodiment 1, wherein the rheology modifier comprises about 0.01% to about 5.0% of the emulsion by weight.

Embodiment 4

The emulsion of any one of the preceding embodiments, wherein the emulsifier comprises about 0.01% to about 10.0% of the emulsion by weight.

Embodiment 5

The emulsion of any one of embodiments 1-3, wherein the emulsifier comprises about 0.01% to about 5.0% of the emulsion by weight.

Embodiment 6

The emulsion of any one of the preceding embodiments, wherein the salt based cosmetic astringent comprises at least about 3.0% of the emulsion by weight.

Embodiment 7

The emulsion of any one of embodiments 1-5, wherein the salt based cosmetic astringent comprises at least about 5.0% of the emulsion by weight.

Embodiment 8

The emulsion of any one of the preceding embodiments, wherein the Glyceryl Stearate comprises at least about 3.0% of the emulsion by weight.

Embodiment 9

The emulsion of any one of embodiments 1-8, wherein the Glyceryl Stearate comprises at least about 4.0% of the emulsion by weight.

Embodiment 10

The emulsion of any one of the preceding embodiments, wherein the salt based cosmetic astringent is selected from the group consisting of: Ammonium and Potassium Alum, Aluminum Triphosphate, Aluminum Glycinate and Aluminum Phenolsulfate, Aldioxa, Aluminum Stearate, Aluminum Sulfate, Aluminum Citrate, Sodium aluminum Phosphate, Sodium Alum, Sodium Aluminum Chlorohydroxy Lactate, Calcium Lactate, Calcium Chloride, Zinc Acetate, Zinc Chloride, Zinc Sulfate, Zinc Lactate, and Zinc Phenolsulfonate.

Embodiment 11

The emulsion of any one of the preceding embodiments, wherein the emulsion is sprayable.

Embodiment 12

An emulsion comprising: (a) a water phase comprising water and a rheology modifier comprising Microcrystalline Cellulose, Cellulose Gum, and Gum Arabic; (b) an oil phase comprising Steareth-2 and an emulsifier selected from the group consisting of: Steareth-20, Steareth-21, and combinations thereof; and (c) a salt based cosmetic astringent comprising at least about 1.0% of the emulsion by weight.

Embodiment 13

The emulsion of embodiment 12, wherein the rheology modifier comprises about 0.01% to about 2.0% of the emulsion by weight.

Embodiment 14

The emulsion of embodiment 12, wherein the rheology modifier comprises about 0.01% to about 5.0% of the emulsion by weight.

Embodiment 15

The emulsion of any one of embodiments 12-14, wherein the emulsifier comprises about 0.01% to about 10.0% of the emulsion by weight.

Embodiment 16

The emulsion of any one of embodiments 12-14, wherein the emulsifier comprises about 0.01% to about 5.0% of the emulsion by weight.

Embodiment 17

The emulsion of any one of embodiments 12-16, wherein the salt based cosmetic astringent comprises at least about 3.0% of the emulsion by weight.

Embodiment 18

The emulsion of any one of embodiments 12-16, wherein the salt based cosmetic astringent comprises at least about 5.0% of the emulsion by weight.

Embodiment 19

The emulsion of any one of embodiments 12-18, wherein the salt based cosmetic astringent is selected from the group consisting of: Ammonium and Potassium Alum, Aluminum Triphosphate, Aluminum Glycinate and Aluminum Phenolsulfate, Aldioxa, Aluminum Stearate, Aluminum Sulfate, Aluminum Citrate, Sodium aluminum Phosphate, Sodium Alum, Sodium Aluminum Chlorohydroxy Lactate, Calcium Lactate, Calcium Chloride, Zinc Acetate, Zinc Chloride, Zinc Sulfate, Zinc Lactate, and Zinc Phenolsulfonate.

Embodiment 20

The emulsion of any one of embodiments 12-19, wherein the emulsion is sprayable

When introducing elements of the present disclosure or the preferred embodiment(s) thereof, the articles "a", "an", "the" and "said" are intended to mean that there are one or more of the elements. The terms "comprising", "including" and "having" are intended to be inclusive and mean that there may be additional elements other than the listed elements. Many modifications and variations of the present disclosure can be made without departing from the spirit and scope thereof. Therefore, the exemplary embodiments described above should not be used to limit the scope of the invention.

What is claimed is:
1. An emulsion comprising:
   a. a water phase comprising water and a rheology modifier comprising Microcrystalline Cellulose and Cellulose Gum;
   b. an oil phase comprising Steareth-2 and Glyceryl Stearate and an emulsifier selected from the group consisting of: Steareth-20, Steareth-21, and combinations thereof; and
   c. a salt based cosmetic astringent in an amount of at least about 1.0% by total weight of the emulsion,
   wherein the salt based cosmetic astringent is selected from the group consisting of: Ammonium and Potassium Alum, Aluminum Triphosphate, Aluminum Glycinate and Aluminum Phenolsulfate, Aldioxa, Aluminum Stearate, Aluminum Sulfate, Aluminum Citrate, Sodium aluminum Phosphate, Sodium Alum, Sodium Aluminum Chlorohydroxy Lactate, Calcium Lactate, Calcium Chloride, Zinc Acetate, Zinc Chloride, Zinc Sulfate, Zinc Lactate, and Zinc Phenolsulfonate.
2. The emulsion of claim 1, wherein the emulsion comprises the rheology modifier in an amount from about 0.01% to about 2.0% by total weight of the emulsion.
3. The emulsion of claim 1, wherein the emulsion comprises the rheology modifier in an amount from about 0.01% to about 5.0% by total weight of the emulsion.
4. The emulsion of claim 1, wherein the emulsion comprises the emulsifier in an amount from about 0.01% to about 10.0% by total weight of the emulsion.
5. The emulsion of claim 1, wherein the emulsion comprises the emulsifier in an amount from about 0.01% to about 5.0% by total weight of the emulsion.
6. The emulsion of claim 1, wherein the emulsion comprises the salt based cosmetic astringent in an amount of at least about 3.0% by total weight of the emulsion.
7. The emulsion of claim 1, wherein the emulsion comprises the salt based cosmetic astringent in an amount of at least about 5.0% by total weight of the emulsion.
8. The emulsion of claim 1, wherein the emulsion comprises the Glyceryl Stearate in an amount of at least about 3.0% by total weight of the emulsion.
9. The emulsion of claim 1, wherein the emulsion comprises the Glyceryl Stearate in an amount of at least about 4.0% by total weight of the emulsion.
10. The emulsion of claim 1, wherein the emulsion is sprayable.

11. An emulsion comprising:
a. a water phase comprising water and a rheology modifier comprising Microcrystalline Cellulose, Cellulose Gum, and Gum Arabic;
b. an oil phase comprising Steareth-2 and an emulsifier selected from the group consisting of: Steareth-20, Steareth-21, and combinations thereof; and
c. a salt based cosmetic astringent in an amount of at least about 1.0% by total weight of the emulsion,
wherein the salt based cosmetic astringent is selected from the group consisting of: Ammonium and Potassium Alum, Aluminum Triphosphate, Aluminum Glycinate and Aluminum Phenolsulfate, Aldioxa, Aluminum Stearate, Aluminum Sulfate, Aluminum Citrate, Sodium aluminum Phosphate, Sodium Alum, Sodium Aluminum Chlorohydroxy Lactate, Calcium Lactate, Calcium Chloride, Zinc Acetate, Zinc Chloride, Zinc Sulfate, Zinc Lactate, and Zinc Phenolsulfonate.

12. The emulsion of claim 11, wherein the emulsion comprises the rheology modifier in an amount from about 0.01% to about 2.0% by total weight of the emulsion.

13. The emulsion of claim 11, wherein the emulsion comprises the rheology modifier in an amount from about 0.01% to about 5.0% by total weight of the emulsion.

14. The emulsion of claim 11, wherein the emulsion comprises the emulsifier in an amount from about 0.01% to about 10.0% by total weight of the emulsion.

15. The emulsion of claim 11, wherein the emulsion comprises the emulsifier in an amount from about 0.01% to about 5.0% by total weight of the emulsion.

16. The emulsion of claim 11, wherein the emulsion comprises the salt based cosmetic astringent in an amount of at least about 3.0% by total weight of the emulsion.

17. The emulsion of claim 11, wherein the emulsion comprises the salt based cosmetic astringent in an amount of at least about 5.0% by total weight of the emulsion.

18. The emulsion of claim 11, wherein the emulsion is sprayable.

* * * * *